(12) United States Patent
Liu et al.

(10) Patent No.: US 8,809,810 B2
(45) Date of Patent: Aug. 19, 2014

(54) MICROARRAY READER BASED ON EVANESCENT WAVE DETECTION

(75) Inventors: Xuanbin Liu, Shanghai (CN); Tao Pan, Shanghhai (CN); Zhenhong Sun, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 17 days.

(21) Appl. No.: 13/697,453

(22) PCT Filed: May 20, 2010

(86) PCT No.: PCT/CN2010/000709
§ 371 (c)(1),
(2), (4) Date: Feb. 4, 2013

(87) PCT Pub. No.: WO2011/143791
PCT Pub. Date: Nov. 24, 2011

(65) Prior Publication Data
US 2013/0130937 A1    May 23, 2013

(51) Int. Cl.
*G01N 21/64* (2006.01)
(52) U.S. Cl.
CPC ..................................... *G01N 21/64* (2013.01)
USPC ..................................................... 250/483.1
(58) Field of Classification Search
CPC ......... G01N 21/64; G01N 33/53; B41J 15/14; C12Q 1/68
USPC ................. 250/483.1, 458.1, 459.1
See application file for complete search history.

(56) References Cited

U.S. PATENT DOCUMENTS

| | | | |
|---|---|---|---|
| 5,015,866 A * | 5/1991 | Hayashi | ........................ 250/548 |
| 5,585,242 A | 12/1996 | Bouma et al. | |
| 5,776,672 A | 7/1998 | Hashimoto et al. | |
| 5,843,651 A | 12/1998 | Stimpson et al. | |

(Continued)

FOREIGN PATENT DOCUMENTS

| CN | 101218496 | 7/2008 |
|---|---|---|
| CN | 101589303 | 11/2009 |

(Continued)

OTHER PUBLICATIONS

"U.S. Appl. No. 10/972,033, Advisory Action mailed Jan. 5, 2011", 3 pgs.

(Continued)

*Primary Examiner* — Kiho Kim
(74) *Attorney, Agent, or Firm* — Schwegman Lundberg & Woessner, P.A.

(57) ABSTRACT

The disclosure relates to a microarray reader that includes a light source which emits light and beam shaping elements positioned near the light source to direct the light. The microarray reader further includes a microarray that is at least formed of an optical substrate and a reaction chamber in contact with the optical substrate. A buffer solution is encapsulated by the optical substrate and the reaction chamber and a holder aligns the microarray relative to the light source such that when light hits the buffer solution molecules in the buffer solution are excited to emit fluorescent light. A temperature control component is thermally engaged with the holder such that the temperature control component adjusts the temperature of the buffer solution. The microarray reader further includes a sensor that receives the fluorescent light emitted by the excited molecules in the buffer solution to generate a signal.

13 Claims, 10 Drawing Sheets

(56) References Cited

U.S. PATENT DOCUMENTS

| | | | |
|---|---|---|---|
| 5,964,998 A * | 10/1999 | Kambara | 204/452 |
| 6,015,674 A | 1/2000 | Woudenberg et al. | |
| 6,207,381 B1 | 3/2001 | Larsson et al. | |
| 6,270,965 B1 | 8/2001 | Kleiber et al. | |
| 6,379,897 B1 | 4/2002 | Weidenhammer et al. | |
| 6,437,345 B1 * | 8/2002 | Bruno-Raimondi et al. | 250/458.1 |
| 6,638,722 B2 | 10/2003 | Ji et al. | |
| 6,995,386 B2 * | 2/2006 | Emoto | 250/576 |
| 7,170,597 B1 | 1/2007 | Rushbrooke et al. | |
| 7,297,961 B2 * | 11/2007 | Kang et al. | 250/458.1 |
| 7,867,767 B2 | 1/2011 | Bedingham et al. | |
| 7,989,220 B2 * | 8/2011 | Lakowicz et al. | 436/525 |
| 8,124,944 B2 | 2/2012 | Zheng et al. | |
| 2001/0020588 A1 | 9/2001 | Adourian et al. | |
| 2002/0102595 A1 | 8/2002 | Davis | |
| 2002/0164629 A1 | 11/2002 | Quake et al. | |
| 2002/0177144 A1 | 11/2002 | Remacle et al. | |
| 2003/0048933 A1 | 3/2003 | Brown et al. | |
| 2003/0124599 A1 | 7/2003 | Chen et al. | |
| 2003/0129770 A1 | 7/2003 | Fernandez | |
| 2003/0148391 A1 | 8/2003 | Salafsky | |
| 2003/0232427 A1 | 12/2003 | Montagu | |
| 2003/0235518 A1 | 12/2003 | Shea et al. | |
| 2004/0009612 A1 | 1/2004 | Zhao et al. | |
| 2004/0125370 A1 | 7/2004 | Montagu | |
| 2004/0217271 A1 | 11/2004 | Staton et al. | |
| 2004/0234114 A1 * | 11/2004 | Amakawa et al. | 382/128 |
| 2005/0014286 A1 * | 1/2005 | Furuki et al. | 436/514 |
| 2005/0026209 A1 | 2/2005 | Vann | |
| 2005/0030535 A1 * | 2/2005 | Rassman et al. | 356/369 |
| 2005/0046848 A1 | 3/2005 | Cromwell et al. | |
| 2005/0118640 A1 * | 6/2005 | Kureshy et al. | 435/7.1 |
| 2005/0186565 A1 | 8/2005 | Malak | |
| 2006/0088844 A1 | 4/2006 | Xu | |
| 2007/0132831 A1 * | 6/2007 | Chu | 347/241 |
| 2008/0117425 A1 * | 5/2008 | Kain | 356/455 |
| 2008/0139395 A1 * | 6/2008 | Imanaka et al. | 506/3 |
| 2009/0088338 A1 | 4/2009 | Liu et al. | |
| 2010/0006774 A1 * | 1/2010 | Ohtsuka et al. | 250/459.1 |
| 2010/0148092 A1 | 6/2010 | Zheng et al. | |
| 2011/0111968 A1 * | 5/2011 | Okura et al. | 506/7 |

FOREIGN PATENT DOCUMENTS

| | | |
|---|---|---|
| DE | 10316159 A1 | 10/2004 |
| EP | 1935496 A1 | 6/2008 |
| JP | 2006-038816 A | 2/2006 |
| JP | 2008-032420 A | 2/2008 |
| NO | WO-2005/118773 A2 | 12/2005 |
| WO | WO-87/06956 A1 | 11/1987 |
| WO | WO-95/26416 A1 | 10/1995 |
| WO | WO-01/57501 A1 | 8/2001 |
| WO | WO-03/062791 A2 | 7/2003 |
| WO | WO-2004/017374 A2 | 2/2004 |
| WO | WO-2006/011346 A1 | 2/2006 |
| WO | WO-2006/135437 A2 | 12/2006 |
| WO | WO-2008/092291 A1 | 8/2008 |
| WO | WO-2011/143791 A1 | 11/2011 |

OTHER PUBLICATIONS

"U.S. Appl. No. 10/972,033, Advisory Action mailed Jun. 28, 2012", 3 pgs.

"U.S. Appl. No. 10/972,033, Advisory Action mailed Dec. 17, 2007", 3 pgs.

"U.S. Appl. No. 10/972,033, Final Office Action mailed Mar. 26, 2012", 21 pgs.

"U.S. Appl. No. 10/972,033, Final Office Action mailed Aug. 18, 2011", 22 pgs.

"U.S. Appl. No. 10/972,033, Final Office Action mailed Sep. 6, 2007", 10 pgs.

"U.S. Appl. No. 10/972,033, Final Office Action mailed Sep. 6, 2007", 11 pgs.

"U.S. Appl. No. 10/972,033, Final Office Action mailed Oct. 3, 2008", 18 pgs.

"U.S. Appl. No. 10/972,033, Final Office Action mailed Oct. 28, 2010", 21 pgs.

"U.S. Appl. No. 10/972,033, Final Office Action mailed Nov. 9, 2009", 21 pgs.

"U.S. Appl. No. 10/972,033, Non Final Office Action mailed Mar. 1, 2011", 21 pgs.

"U.S. Appl. No. 10/972,033, Non Final Office Action mailed Mar. 27, 2007", 12 pgs.

"U.S. Appl. No. 10/972,033, Non-Final Office Action mailed Mar. 11, 2008", 11 pgs.

"U.S. Appl. No. 10/972,033, Non-Final Office Action mailed Mar. 31, 2010", 22 pgs.

"U.S. Appl. No. 10/972,033, Non-Final Office Action mailed Apr. 2, 2009", 17 pgs.

"U.S. Appl. No. 10/972,033, Response filed Jan. 5, 2009 to Final Office Action mailed Oct. 3, 2008", 9 pgs.

"U.S. Appl. No. 10/972,033, Response filed Jan. 22, 2007 to Restriction Requirement mailed Dec. 20, 2006", 5 pgs.

"U.S. Appl. No. 10/972,033, Response filed Feb. 9, 2010 to Final Office Action mailed Nov. 9, 2009", 10 pgs.

"U.S. Appl. No. 10/972,033, Response filed May 18, 2011 to Non Final Office Action mailed Mar. 1, 2011", 12 pgs.

"U.S. Appl. No. 10/972,033, Response filed May 24, 2012 to Final Office Action mailed Mar. 26, 2012", 12 pgs.

"U.S. Appl. No. 10/972,033, Response filed Jun. 5, 2008 to Non Final Office Action mailed Mar. 11, 2008", 8 pgs.

"U.S. Appl. No. 10/972,033, Response filed Jun. 21, 2007 to Non Final Office Action mailed Mar. 27, 2007", 6 pgs.

"U.S. Appl. No. 10/972,033, Response filed Jun. 29, 2010 to Non Final Office Action mailed Mar. 31, 2010", 11 pgs.

"U.S. Appl. No. 10/972,033, Response filed Jul. 1, 2009 to Non Final Office Action mailed Apr. 2, 2009", 10 pgs.

"U.S. Appl. No. 10/972,033, Response filed Oct. 18, 2011 to Non Final Office Action mailed Aug. 18, 2011", 11 pgs.

"U.S. Appl. No. 10/972,033, Response filed Dec. 6, 2007 to Final Ofice Action mailed Sep. 6, 2007", 6 pgs.

"U.S. Appl. No. 10/972,033, Response filed Dec. 28, 2010 to Final Office Action mailed Oct. 28, 2010", 11 pgs.

"U.S. Appl. No. 10/972,033, Restriction Requirement mailed Dec. 20, 2006", 5 pgs.

"U.S. Appl. No. 12/325,913, Final Office Action mailed Aug. 15, 2011", 28 pgs.

"U.S. Appl. No. 12/325,913, Non Final Office Action mailed Mar. 30, 2011", 22 pgs.

"U.S. Appl. No. 12/325,913, Response filed Jan. 26, 2011 to Restriction Requirement mailed Dec. 29, 2010", 6 pgs.

"U.S. Appl. No. 12/325,913, Response filed Jun. 30, 2011 to Non Final Office Action mailed Mar. 30, 2011", 10 pgs.

"U.S. Appl. No. 12/325,913, Restriction Requirement mailed Dec. 29, 2010", 6 pgs.

"U.S. Appl. No. 12/325,913, Response filed Nov. 14, 2011 to Final Office Action mailed Aug. 15, 2011", 10 pgs.

"U.S. Appl. No. 12/522,188, Final Office Action mailed Oct. 5, 2011", 10 pgs.

"U.S. Appl. No. 12/522,188, Non Final Office Action mailed May 12, 2011", 9 pgs.

"U.S. Appl. No. 12/522,188, Non Final Office Action mailed Dec. 16, 2010", 7 pgs.

"U.S. Appl. No. 12/522,188, Notice of Allowance mailed Oct. 19, 2011", 5 pgs.

"U.S. Appl. No. 12/522,188, Response filed Mar. 1, 2011 to Non Final Office Action mailed Dec. 16, 2010", 8 pgs.

"U.S. Appl. No. 12/522,188, Response filed Oct. 10, 2011 to Final Office Action mailed Oct. 5, 2011", 7 pgs.

"U.S. Appl. No. 12/522,188, Response filed Jul. 12, 2011 to Non Final Office Action mailed May 12, 2011", 8 pgs.

"Chinese Application Serial No. 200780049987.4, Office Action mailed Jan. 12, 2011", 3 pgs.

"Chinese Application Serial No. 200580044154, First Office Action mailed Apr. 30, 2010", (w/ English Translation), 12 pgs.

(56) References Cited

OTHER PUBLICATIONS

"Chinese Application Serial No. 200580044154, Response filed Aug. 5, 2011 to Second Office Action mailed May 25, 2011", (w/ English Translation of Claims), 8 pgs.

"Chinese Application Serial No. 200580044154, Response filed Nov. 2, 2010 to Office Action dated Apr. 30, 2010", (w/ English Translation of Claims), 11 pgs.

"Chinese Application Serial No. 200580044154, Second Office Action mailed May 25, 2011", (w/ English Translation), 6 pgs.

"Chinese Application Serial No. 200780049987.4, First Office Action mailed Apr. 26, 2010", (w/ English Translation), 16 pgs.

"Chinese Application Serial No. 200780049987.4, Response filed Feb. 17, 2011 to Office Action dated Jan. 12, 2011", (w/ English Translation of Claims), 4 pgs.

"Chinese Application Serial No. 200780049987.4, Response filed Jul. 25, 2011 to Office Action mailed May 11, 2011", (w/ English Translation of Claims), 5 pgs.

"Chinese Application Serial No. 200780049987.4, Office Action issued May 11, 2011", (w/ English Translation), 7 pgs.

"International Application Serial No. PCT/CN2007/000020, International Preliminary Report on Patentability dated Jul. 21, 2009", 7 pgs.

"International Application Serial No. PCT/CN2007/000020, International Search Report mailed Oct. 25, 2007", 6 pgs.

"International Application Serial No. PCT/CN2007/000020, Written Opinion mailed Oct. 25, 2007", 6 pgs.

"International Application Serial No. PCT/CN2010/000709, International Preliminary Report on Patentability mailed Nov. 29, 2012", 7 pgs.

"International Application Serial No. PCT/CN2010/000709, International Search Report mailed Oct. 8, 2010", 7 pgs.

"International Application Serial No. PCT/CN2010/000709, Written Opinion mailed Oct. 8, 2010", 4 pgs.

"International Application Serial No. PCT/US2005/037833, International Search Report mailed Jan. 22, 2007", 4 pgs.

"International Application Serial No. PCT/US2005/037833, Written Opinion mailed Jan. 22, 2007", 8 pgs.

"Machine Translation of JP 2006-038816A, published Feb. 9, 2006", 36 pgs.

Afanassiev, V., et al., "Preparation of DNA and protein micro arrays on glass slides coated with an agarose film", *Nucleic Acids Research*. 28(12), (2000), e66 (i-v).

Bustin, S. A., et al., "Quantification of mRNA using real-time reverse transcription PCR (RT-PCR): trends and problems", *Journal of Molecular Endocrinology*, 29, (2002), 23-39.

Liu, Xiaojing, et al., "A Fiber-Optic Evanescent Wave DNA Biosensor Based on Novel Molecular Beacons", *Analytical Chemistry*, 71(22), (Nov, 15, 1999), 5054-5059.

Peter, C., et al., "Optical DNA-sensor chip for real-time detection of hybridization events", *Fresenius Journal of Analytical Chemistry*, 317(2), (2001), 120-127.

Soper, S. A., et al., "Nanoliter-scale sample preparation methods directly coupled to polymethylmethacrylate-based microchips and gel-filled capillaries for the analysis of oligonucleotides", *Journal of Chromatography A*, 853(1-2), (Aug. 20, 1999), 107-120.

Szuhai, K., et al., "A Novel Strategy for Human Papillomavirus Detection and Genotyping with SybrGreen and Molecular Beacon Polymerase Chain Reaction", *American Journal of Pathology*, 159(5), (2001), 1651-1660.

Tolley, S. E., et al., "Single-chain polymorphism analysis in long QT syndrome using planar waveguide fluorescent biosensors", *Analytical Biochemistry*, 315(2), (Apr. 15, 2003), 223-237.

\* cited by examiner

MICROARRAY READER BASED ON EVANESCENT WAVE DETECTION

CROSS-REFERENCE TO RELATED APPLICATIONS

This application is a national stage of PCT/CN2010/000709.

TECHNICAL FIELD

Embodiments of the present invention relate to a microarray reader based on evanescent wave detection. More specifically, embodiments of the present invention relate to a microarray reader for real-time PCR microarray based on evanescent wave detection.

BACKGROUND

Microarray readers conventionally used are based on florescent label, confocal microscopy and evanescent field. Examples include florescent scanning confocal microscopy and total internal reflection (TIR) fluorescent microscopy. These readers have a small field of view and require precise moving parts to scan the array, which leads to costly and slow reading. One approach includes exciting the whole probe array by expanding light source with uniform intensity distribution. However, lower sensitivity results due to the lower excitation.

Microarray readers with waveguide structures can produce high sensitivity and are free of moving parts. These readers are not suitable for disposable chip applications though, because of the high costs of waveguide fabrication and rigid alignment and coupling requirements. None of the existing microarray readers can meet the need of real-time PCR microarray detection due to the unique requirements in temperature control and sampling synchronization.

One drawback with existing microarray readers is that there is often optical scattering due to improper positioning of the microarray to be tested. FIG. 6 shows an example system where there are four points on the lower surface of an optical substrate (points A, B, C, D). Point A and point D represent the edge of an optical substrate while point B and point C represent the edge of a buffer solution.

If each microarray chip is positioned differently relative to the emitted light, the resulting starting point of each scan would be different. As an example, strong optical scattering may occur at left edge of the optical substrate (point A) or a strong optical scattering may occur at the right edge of the optical substrate (point D) when the optical substrate and/or the buffer solution is misaligned relative to the emitted light. Both scenarios may cause the scattering signal to be so strong that useful microarray signals become unclear. In addition, a misaligned optical substrate may cause only part of buffer solution to be illuminated during scanning such that a CCD camera (or other sensor) only captures a partial image of the reaction chamber.

Another drawback with existing microarray readers is that the microarray is often inadequately secured such that fringe-shaped backgrounds are generated in CCD images. Linear fringes may appear in CCD images even when the microarray chip is correctly positioned on the temperature control plate. One cause of linear fringes is due to vibration of the microarray during the scanning process as the laser is maneuvered on a motor-driven supporting stage.

The linear fringes blur the image and influence the gray scale of pixels in the image such that the signal/noise ratio is decreased. The decrease in signal/noise ratio may cause the signal to be hard to recognize resulting in unacceptable errors.

Still another drawback with existing microarray readers is that the microarray may be heated non-uniformly. During a typical scanning operation, the temperature control plate is placed against the microarray. The temperature control plate is typically larger than the microarray such that there is a large temperature difference between different regions of the microarray. This large temperature difference may cause the amplification/hybridization reaction to fail because the reaction is conducted at a non-uniform temperature.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Embodiments of the present invention relate a microarray reader comprising: a light source, beam shaping elements positioned near the light source, a moving stage supporting one or more of the light source and beam shaping elements, an optical substrate supporting an immobilized microarray, a reaction chamber in contact with the optical substrate and encapsulating a buffer solution, a heating/cooling component in contact with the reaction chamber, a synchronization circuit, an optical filter and an imaging sensor positioned near the optical filter.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the present invention relate to a microarray reader for real-time PCR microarray analysis with evanescent wave detection. The microarray reader is low cost, reliable and can be utilized in a number of microarray configurations. The microarray reader also has convenient control, fast reading and high sensitivity. The microarray reader includes temperature control as well as a sampling synchronization circuit. The reader analyzes the signal by line scanning mode and utilizes intensity calibration and uniformity calibration. The optical substrate may be used not only to support the microarray, but also as the medium for total internal reflection. A reflective or absorptive coating may be partially applied to the substrate to decrease scattering noise and also serve as a position marker.

Figure 1:
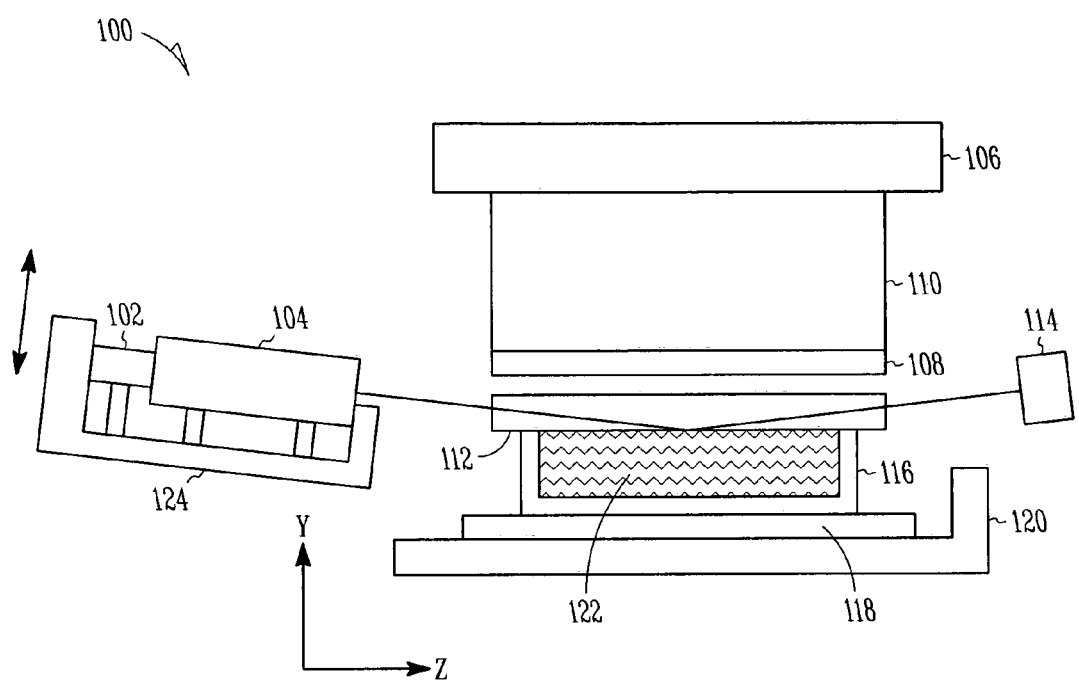
FIG. 1 illustrates a cross-sectional view of a microarray reader 100 based on evanescent wave detection, according to some embodiments.

Referring to FIG. 1, a cross-sectional view of a microarray reader 100 based on evanescent wave detection is shown, according to some embodiments. A linear translation stage 124 may support a line shape output light source 102, such as a laser. The wavelength of the light source 102 may be chosen to be in a range to activate the fluorescent tag. The light source 102 may be reshaped by cylindrical lenses 104 (beam shaping elements) before contacting substrate 112. Contacting may include entering the substrate 112, for example. The cylindrical lenses 104 may be diffraction optical elements or diffusing optical elements, for example.

The light source 102, cylindrical lenses 104 and linear translation stage 124 may make up a line scanning excitation system. The substrate 112 may be an optical substrate, such as glass or a polymer, for example. The substrate 112 may be very thin to decrease thermal capacity and meet the demands of rapid temperature control. The substrate 112 may be about 1 mm to about 3 mm thick, for example. The substrate 112 may be manufactured of a low autofluorescent material at the excitation wavelength.

Figure 3:
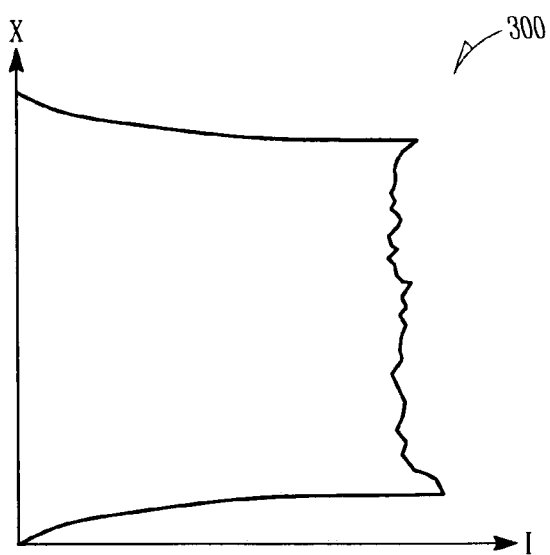
FIG. 3 illustrates a graphical view of an intensity profile of a line shape output light source, according to some embodiments.

The line scanning excitation system may sustain uniform intensity (as shown in FIG. 3). Uniform line scanning with uniformity calibration may be applied to overcome the lower speed for spot scanning, for example. To get flexible and convenient coupling, direct coupling may be applied, for example. Position variation of excitation may be adjusted by feedback control, for example. A synchronization circuit may be utilized by the line scanning excitation system to synchronize sampling, for example.

The substrate 112 may contact a reaction chamber 116, encapsulating a buffer solution 122 and making up a real-time PCR microarray reaction system. The refractive index of the substrate 112 may be higher than the buffer solution 122, for example. The substrate may be glued to the reaction chamber 116, for example. The fluorescent tag may be imaged in an imaging sensor 106, such as a cooled CCD camera 106 by imaging lenses 110. An optical filter 108 between the substrate 112 and image lenses 110 may be utilized to block the exciting light and pass the fluorescence. In contact with the reaction chamber 116, a heating/cooling element 118 on a stage 120 may be utilized for heating, cooling or stabilization of the reaction system. The element 118 may be a TEC temperature control plate, for example. Variation of any light source intensity may be monitored by detector 114, such as a photo-electric detector.

Figure 2:
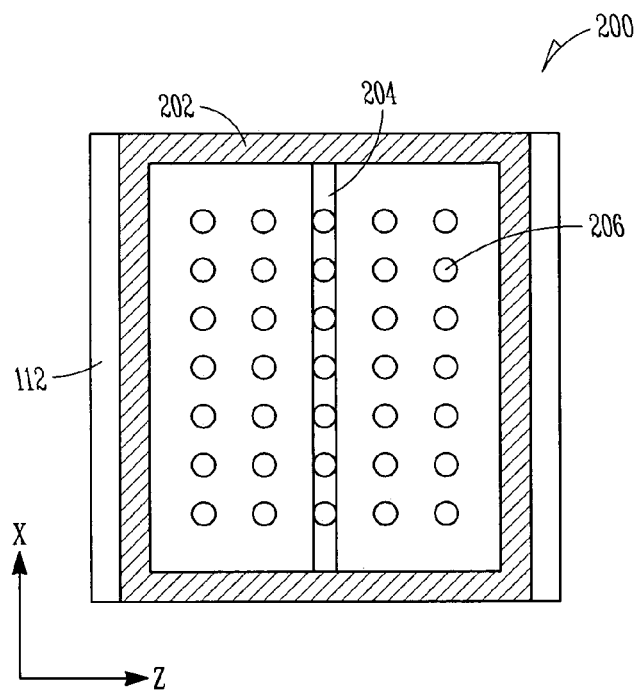
FIG. 2 illustrates a perspective view of an optical substrate 200, according to some embodiments.

Referring to FIG. 2, a perspective view of an optical substrate 200 is shown, according to some embodiments. To prevent any scattering caused by an adhesive, a multi-layer reflective or absorptive coating 202 may be coated on the adhesion area on the bottom side of the substrate 200. The coating 202 may also serve as a position marker, for example. Towards the bottom side of the substrate 200, total internal reflection may occur where probe array 206 may be immobilized on the surface. The optical substrate 200 may not only serve as the solid support for the microarray, but also as the optical dense media for the total internal reflection, for example. A column of array probe combined with florescent labeled target may be excited by line shape 204 evanescent field. To decrease the scattering at the optical substrate surface 200, facets of the substrate 112 may be fine polished. For example, four facets may be fine polished. For example, the left side surface, right side surface, upper side surface and bottom side surface may be polished. The surface quality of the optical substrate 200 may be better than 40-20 scratch-dig MIL-O-13830, for example.

Figure 4:
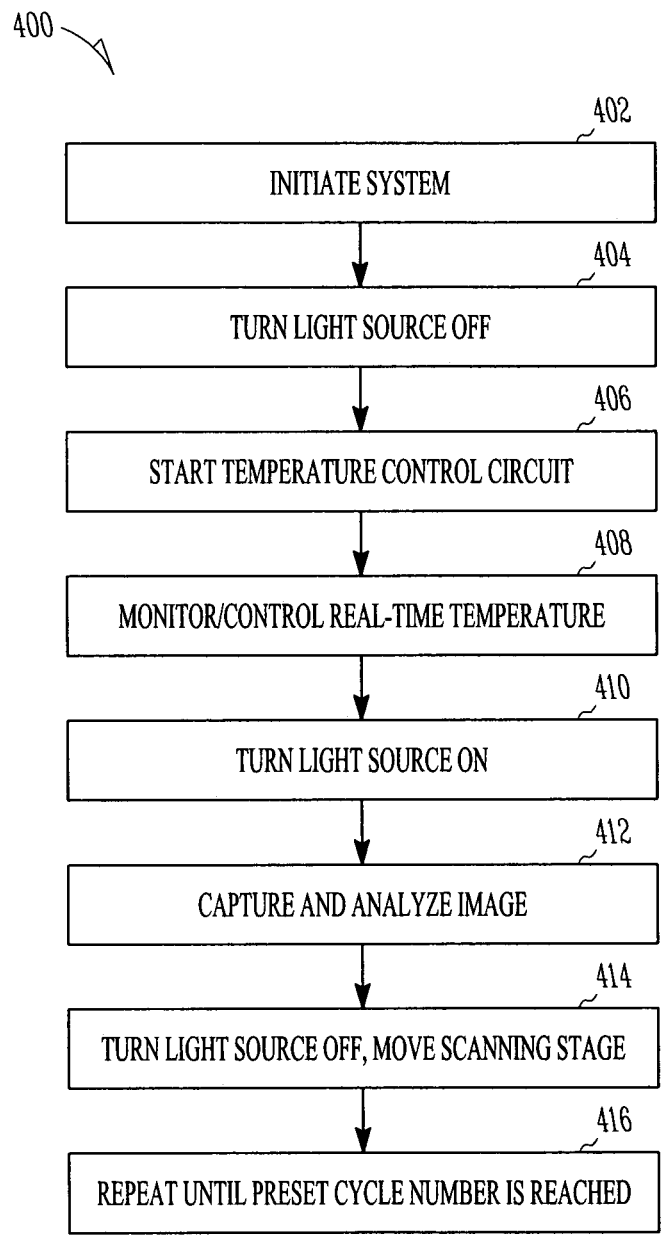
FIG. 4 illustrates a block flow diagram of a method of reading a microarray, according to some embodiments.

Referring to FIG. 4, a block flow diagram of a method 400 of reading a microarray is shown, according to some embodiments. The microarray reader system may be initiated 402, the light source may be turned off 404 before imaging capture and temperature control circuit initiated 406. The real-time temperature control may be monitored 408 during the entire reading process. The light source may be turned back on 410. Image capture and analysis 412 may be executed after the temperature reaches the preset sampling temperature. The light source may then be turned off and scanning station moved 414 to the next position. Steps 408 through 414 may be repeated until the preset cycle number has been reached 416.

System initiation 402 may include light source intensity calibration, line uniformity calibration, light source orientation, temperature parameter configuration, image setup or combinations thereof. Image analysis may be used for calibration, for example.

Figure 5:
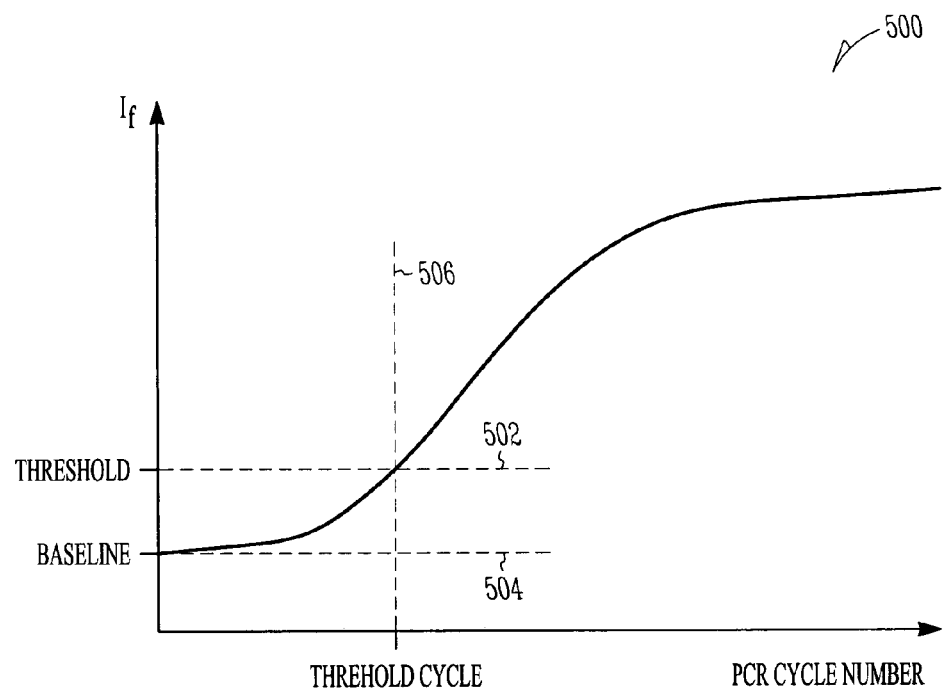
FIG. 5 illustrates a graphical view of an exemplary fluorescent labeled PCR signal curve, according to some embodiments.
Figure 6:
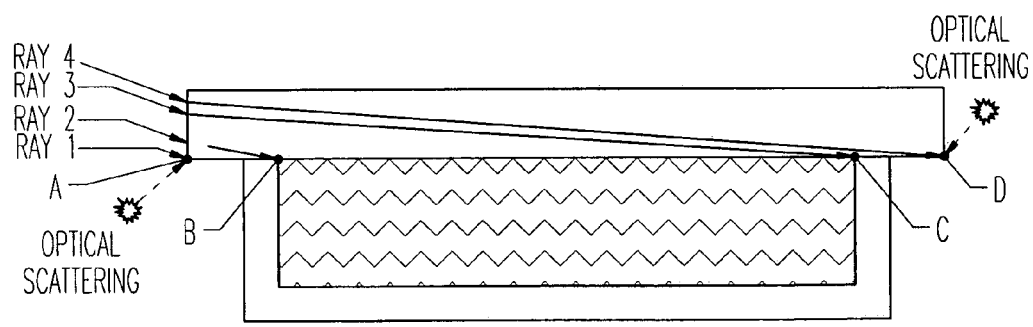
FIG. 6 illustrates a schematic sectional view of an example microarray that may be used in a microarray reader.

Referring to FIG. 5, a graphical view of an exemplary fluorescent labeled PCR signal curve 500 is shown, according to some embodiments. A fluorescent labeled PCR signal curve is plotted versus the PCR cycle number. The background florescent baseline 504 marks the beginning of the PCR cycle. At the threshold cycle 506, florescent signal greatly increases versus time. The log of the initial target substance number is proportional to the threshold cycle 506. The number of target substance may be deduced from threshold cycle analysis.

The microarray of the embodiments of the present invention may be utilized with the microarray procedure of the following example, such as in copending U.S. patent application Ser. No. 10/972,033, filed Oct. 22, 2004. A PCR buffer contains fluorescently-tagged dNTPs, i.e., dNTPs having a fluorescent dye molecule attached to them, so that upon completion of each PCR cycle, the amplicons produced are fluorescently tagged. The amplicons of the target DNA are then localized, using probe strands of DNA known as oligoprobes. The oligoprobes have the complementary, nucleotide sequence as the target DNA. The oligopobes are tethered to a substrate surface in a known, two-dimensional pattern, with the substrate surface forming part of the reaction cell containing the PCR ingredients.

During the annealing and extension phases of the PCR process, the fluorescently-tagged, target amplicons hybridize to their corresponding oligoprobes. The hybridized, fluorescently tagged target amplicons are then illuminated with an evanescent wave of light of the appropriate wave-length to activate the fluorescent dye molecules of the tagged dNTPs. This evanescent wave decays exponentially in power after entering the reaction cell via the substrate surface to which the oligoprobes are tethered, with an effective penetration range of about 300 nm. This means that the evanescent wave penetrates far enough into the reaction cell to activate the fluorescently tagged amplicons hybridized to those oligopobes, but that it does not activate the fluorescently tagged dNTPS in solution in the main body of the reaction cell. By monitoring the strength of the fluorescence at various locations on the substrate surface, the current abundance of amplicons of the corresponding, target DNA can be determined. This may be done in real time as the PCR reaction progresses, and the results used to obtain a quantitative measure of the abundance of a specific target in the original sample, in a manner analogous to the real time PCR calculation.

Figure 7:
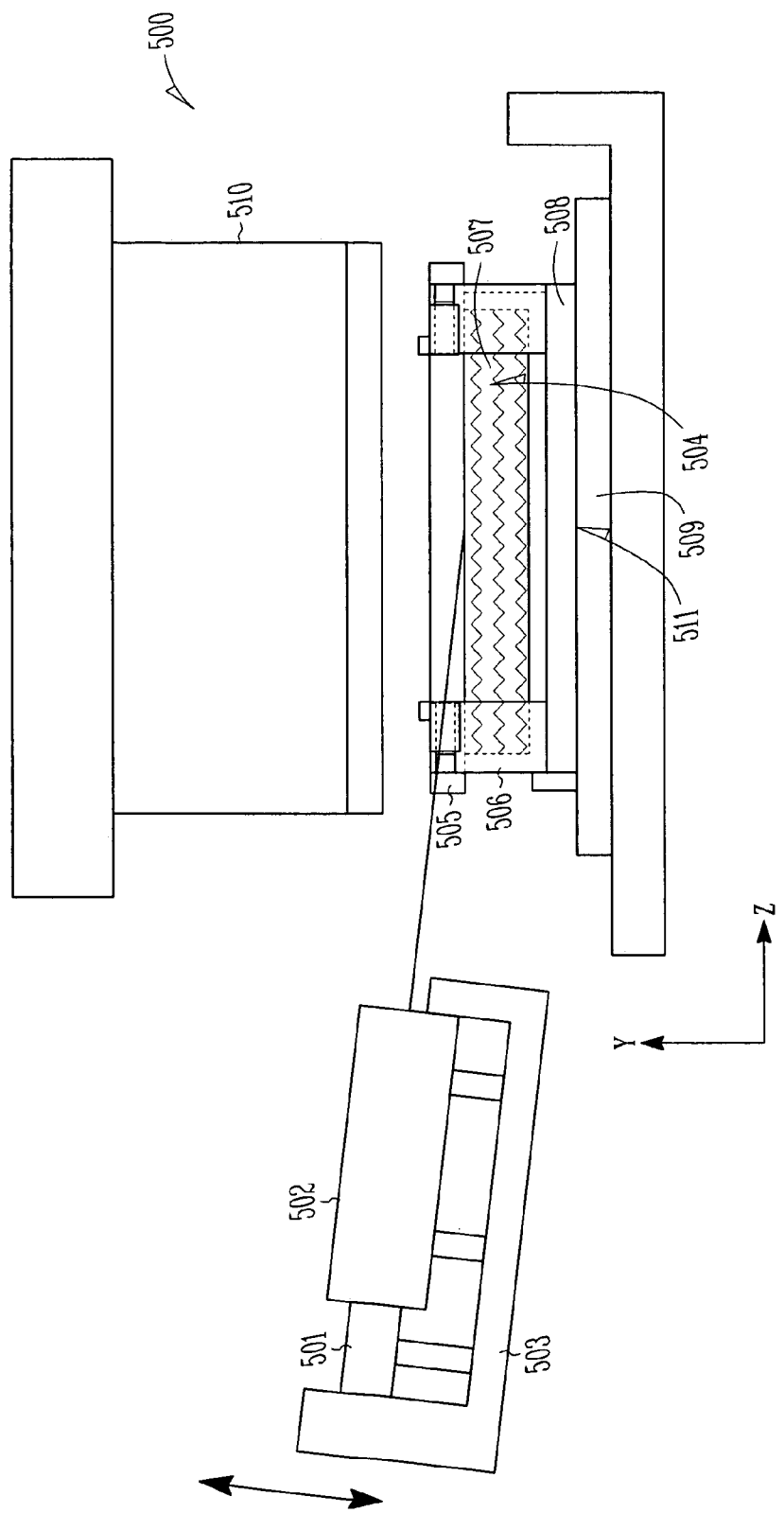
FIG. 7 illustrates a schematic sectional view of another microarray reader.
Figure 8:
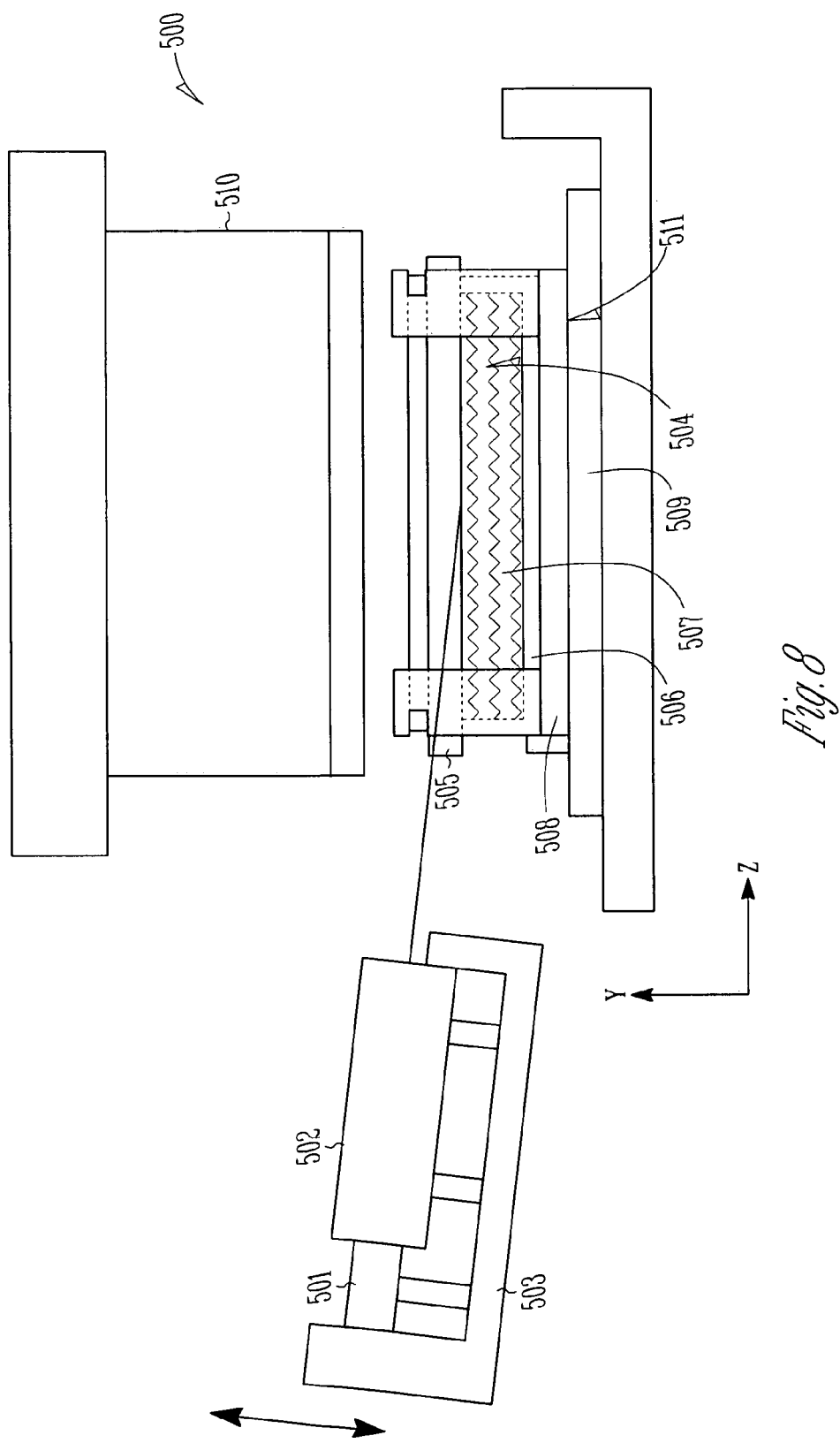
FIG. 8 illustrates a schematic sectional view of yet another microarray reader.
Figure 9:
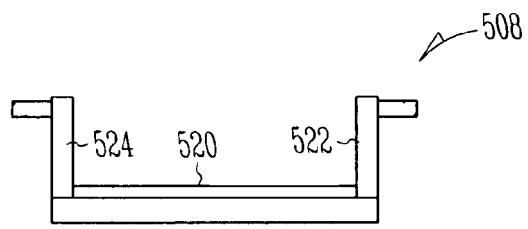
FIG. 9 is front view of an example holder that may be used in the microarray reader shown FIG. 7.
Figure 11:
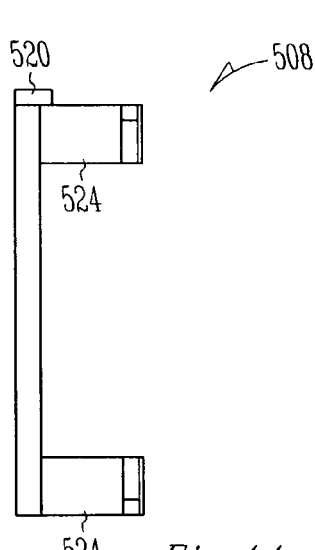
FIG. 11 is side view of the example holder shown FIG. 9.
Figure 10:
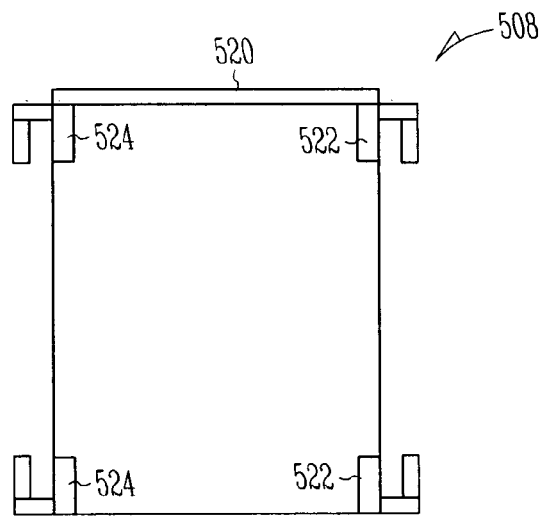
FIG. 10 is top view of the example holder shown FIG. 9.
Figure 12:
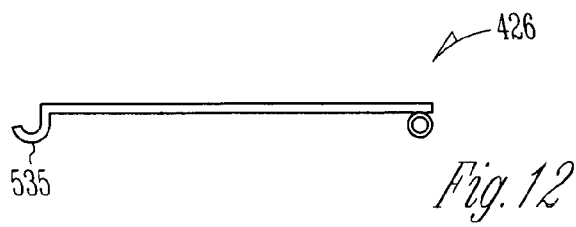
FIG. 12 is side view of an example pin that may be used with the holder shown FIGS. 9-11 to secure a microarray.
Figure 13:
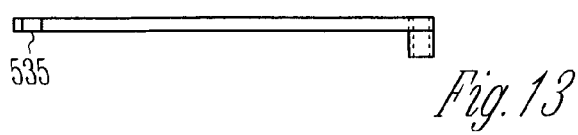
FIG. 13 is top view of the example pin shown FIG. 12.
Figure 14:
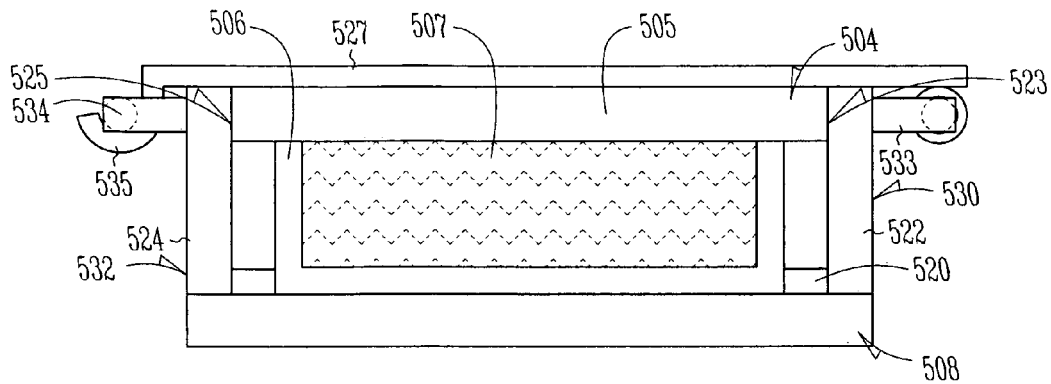
FIGS. 14 and 15 are schematic side and top views of the example holder shown FIGS. 9-11 and pin shown FIGS. 12-13 securing a microarray.

FIGS. 7-21 illustrate other example microarray readers 500 and example components that are used in the microarray readers 500. As shown in FIGS. 7 and 8, the microarray reader 500 includes a light source 501 that emits light and beam shaping elements 502 positioned near the light source 501 to direct the light. A moving stage 503 supports the light source 501 and beam shaping elements 502.

The microarray reader 500 further includes a microarray 504 that is at least formed of an optical substrate 505 and a reaction chamber 506 in contact with the optical substrate 505. A buffer solution 507 is encapsulated by the optical substrate 505 and the reaction chamber 506 and a holder 508 aligns the microarray 504 relative to the light source 501 such that when light hits the buffer solution 507 certain molecules in the buffer solution 507 are excited to emit fluorescent light. A temperature control component 509 is thermally engaged with the holder 508 such that the temperature control component 509 adjusts the temperature of the buffer solution 507 and sensor 510 receives the fluorescent light emitted by the excited molecules in the buffer solution 507 to generate a signal.

In some embodiments, a PCR reaction occurs within the buffer solution 507. In addition, the sensor 510 may include a CCD camera that receives the fluorescent light emitted by the excited molecules in the buffer solution 507.

The holder 508 may include a bottom surface 511 such that the temperature control component 509 engages the entire bottom surface 511 of the holder 508. In some embodiments, the holder 508 may be bonded to the temperature control component 509 with thermally conductive glue. One example glue that may be used to bond the holder 508 to the temperature control component 509 is SE 9184 WHITE RTV manufactured by Dow Corning Corp.

In some embodiments, the holder 508 may be made of a material with a high coefficient of thermal conductivity that serves to help maintain uniform temperature across the microarray 504. Maintaining a uniform temperature of the microarray 504 is especially important when a PCR amplification and hybridization reaction is performed within the reaction chamber 506. The holder 508 may be made from a material that has a (i) high thermal conductivity; (ii) high thermal stability; (iii) low coefficient of thermal expansion; and (iv) sufficient hardness.

In some embodiments, the melting point of the holder 508 material is higher than 100 degrees Centigrade such that the holder 508 does not distort at temperatures near 100 degrees. Some example materials for the holder 508 include, but are not limited to: copper, aluminum, sliver, iron, steel, conductive plastics (e.g., PPS, PP, ABS, PC, PA, LCP, PEEK) or a combination of any of the above. In addition, the holder 508 may be black (e.g., by painting, anodizing, etc.) to reduce optical scattering.

A highly conformable and thermally conductive interface material may be placed between the holder 508 and the microarray 504 to mitigate the effect of any air gaps and rough surfaces that may be between the holder 508 and the microarray 504 and to provide an effective thermal interface between the holder 508 and the microarray 504. One example material that may be used between the holder 508 and the microarray 504 is a Gap Pad product manufactured by Berquist Company.

FIGS. 9-11, 14-17 and 20, 21 show example embodiments where the holder 508 includes a first baffle 520 that engages a first side 521 of the microarray 504 when the microarray 504 is appropriately positioned within the holder 508. As shown most clearly in FIGS. 14-15 and 20-21, the first baffle 520 engages the reaction chamber 506 and/or the optical substrate 505 when the microarray 504 is appropriately positioned within the holder 508.

In some embodiments, the holder 508 includes a second baffle 522 that engages a second side 523 of the microarray 504 when the microarray 504 is appropriately positioned within the holder 508. The second baffle 522 may engage the optical substrate 505 when the microarray 504 is appropriately positioned within the holder 508.

In some embodiments, the holder 508 includes a third baffle 524 that engages a third side 525 of the microarray 504 when the microarray 504 is appropriately positioned within the holder 508. The third baffle 524 may engage the optical substrate 505 when the microarray 504 is appropriately positioned within the holder 508.

When the microarray 504 is appropriately placed into the holder 508, the first, second and third baffles 520, 522, 524 serve to align the microarray 504 relative to the light source 501 and thereby reduce the risk of undesirable scattering during optical scanning. Depending on the configuration of the holder 508, the first, second and third baffles 520, 522, 524 may engage the optical substrate 505 when the microarray 504 is appropriately positioned within the holder 508. It should be noted that in other embodiments, only one or two of the first, second and third baffles 520, 522, 524 may engage the reaction chamber 506 and/or the optical substrate 505 of the microarray 504.

In some embodiments, the microarray reader 500 further includes a pin 526 that compresses the microarray 504 against the holder 508. In the illustrated example embodiments, the pin 526 engages the holder 508 and the optical substrate 505.

Since the microarray 504 is fixed to the sample holder 508 by the pin 526, many of vibrations that would otherwise be transferred to the microarray 504 are mitigated. Reducing the effect of vibrations on the microarray 504 significantly decreases the detected noise level and as a result increases the signal/noise ratio of the microarray reader 500.

Figure 15:
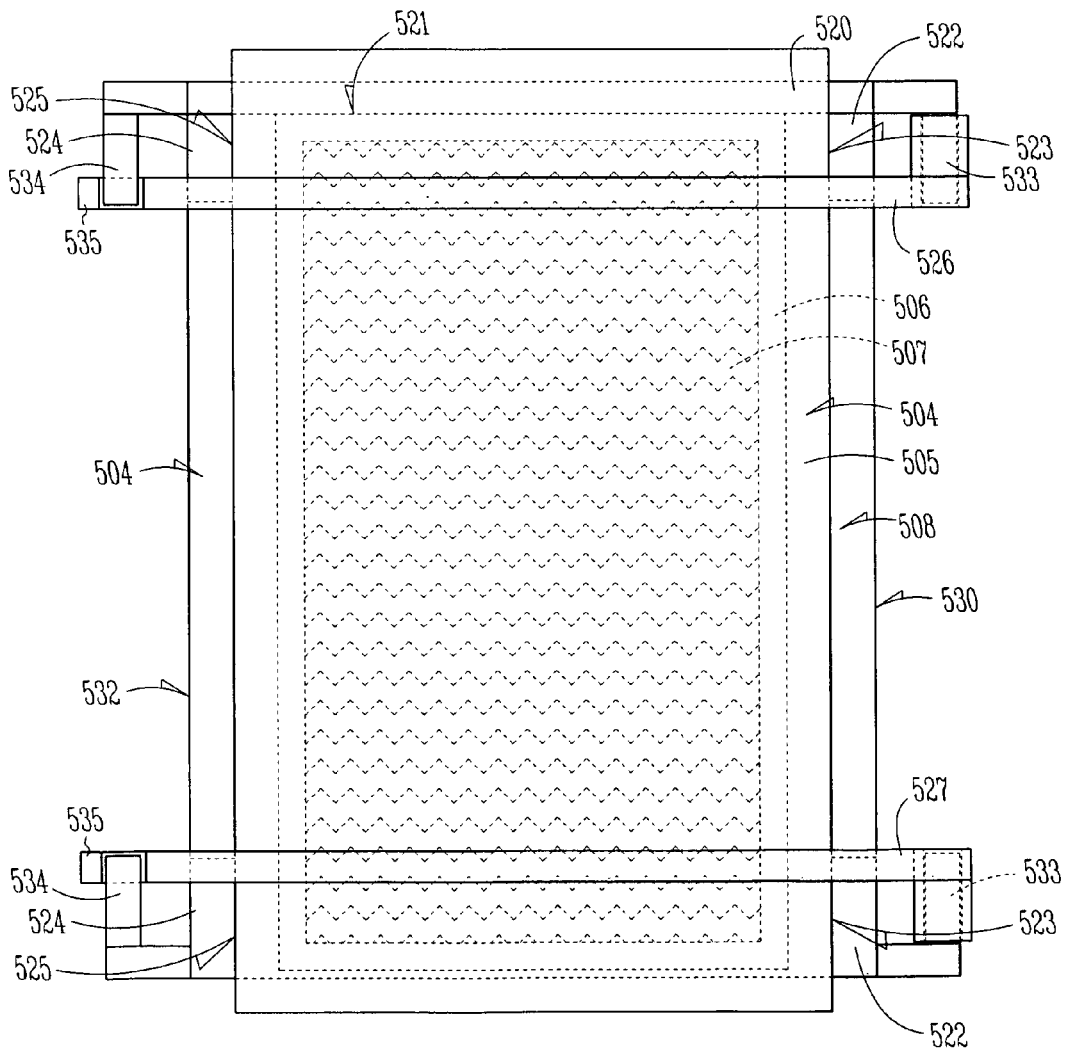
Figure 16:
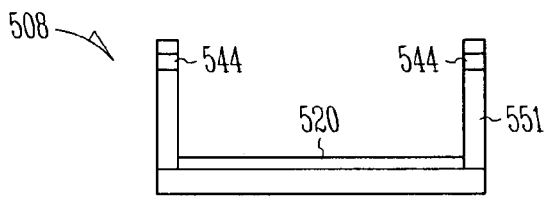
FIG. 16 is front view of another example holder that may be used in the microarray reader shown FIG. 8.
Figure 17:
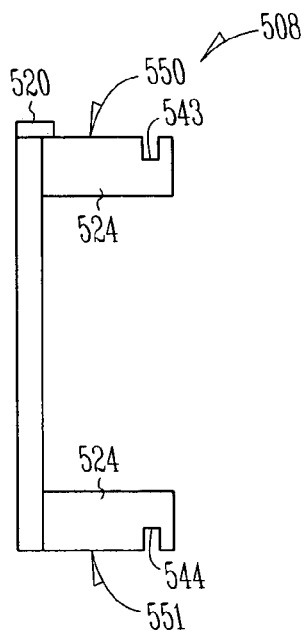
FIG. 17 is top view of the example holder shown FIG. 16.
Figure 18:
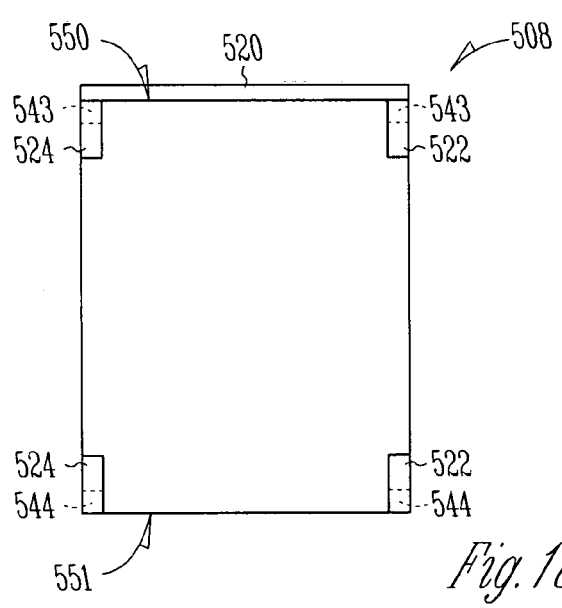
FIG. 18 is side view of the example holder shown FIG. 16.

As shown in FIG. 15, the microarray reader 500 may further include at least one additional pin 527 that compresses the microarray 504 against the holder 508. In some embodiments, the pins 526, 527 may be rotatably connected to a first side 530 of the holder 508 and engaged with a projection on an opposing second side 532 of the holder 508.

In the illustrated example embodiment, the holder 508 includes cylindrical projections 533 on the first side 530 of the holder 508 and the pins 526, 527 each include a cylindrical opening that receives the cylindrical projections 533 such that the pins 526, 527 are rotatably connected to the first side 530 of the holder 508. The holder 508 may also include a protrusion 534 on the opposing second side 532 of the holder 508 such that a hook 535 on each of the pins 526, 527 engages the respective protrusions 534 to compress the microarray 504 against the holder 508.

Figure 19:
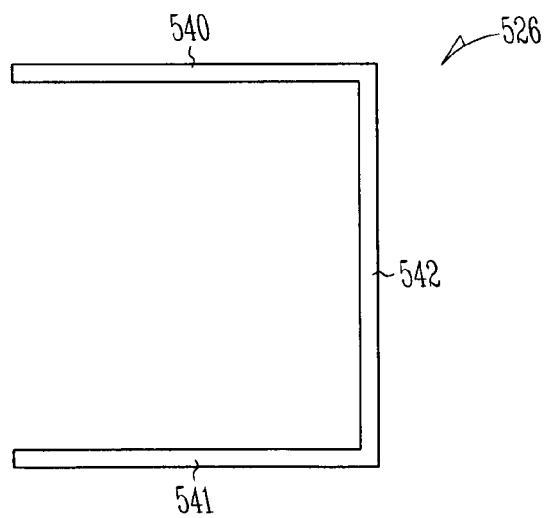
FIG. 19 is top view of an example pin that may be used with the holder shown FIGS. 16-18 to secure a microarray.
Figure 20:
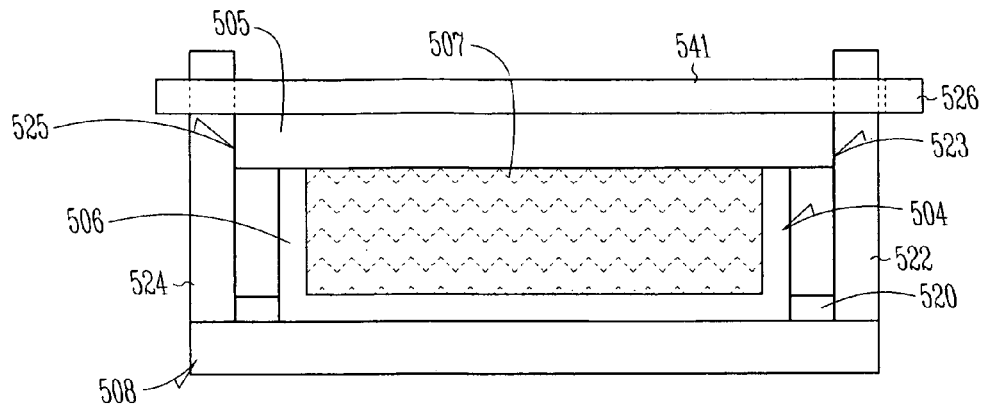
FIGS. 20 and 21 are schematic side and top views of the example holder shown FIGS. 16-18 and pin shown FIG. 19 securing a microarray.
Figure 21:
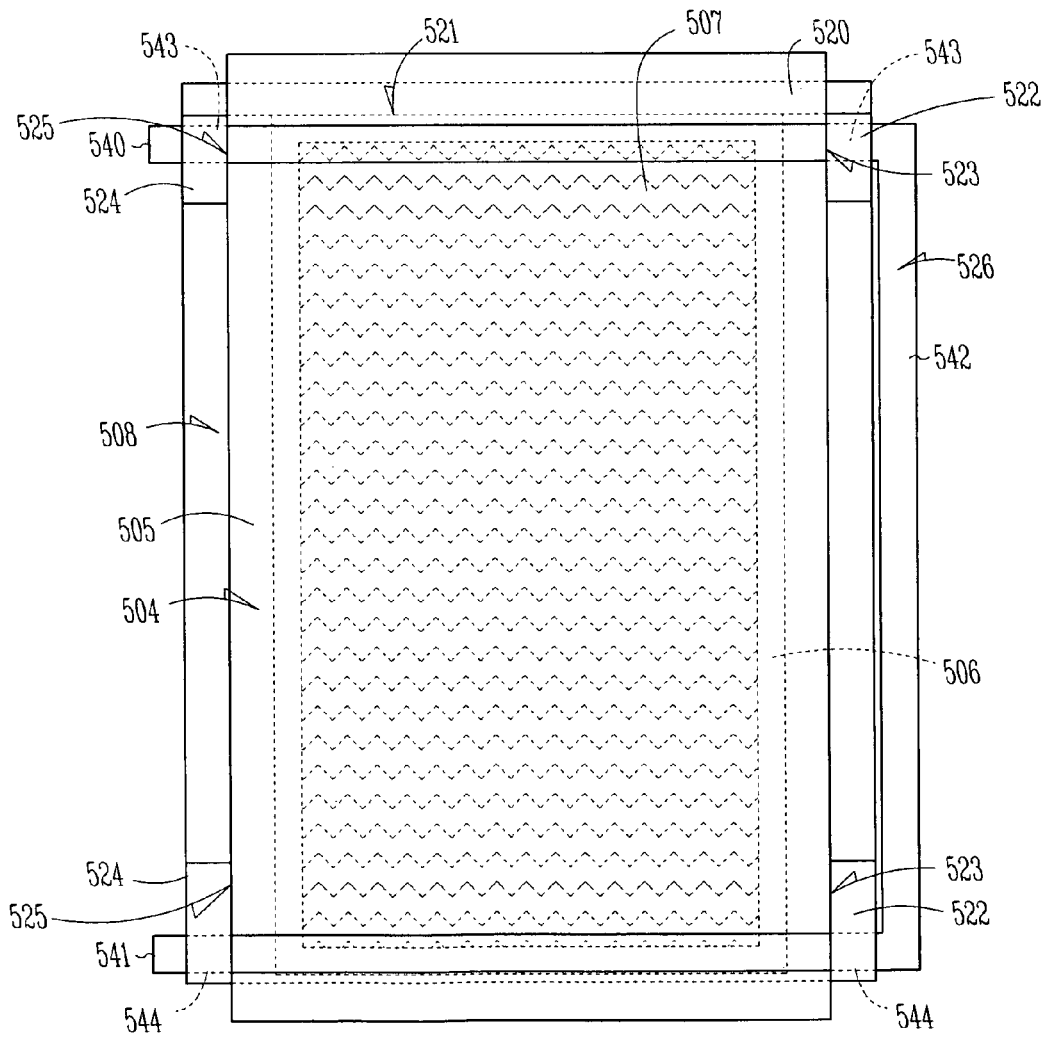

As shown in FIGS. 19 and 21, the pin 526 may also be a U-shaped member. In the illustrated example embodiment, the U-shaped member 526 includes a first leg 540, a second leg 541 and a section 542 that extends between the first leg 540 and the second leg 541. The holder 508 may include recesses 543 on a first side 550 of the holder 508 and recesses 544 on second side 551 of the holder (see, e.g., FIGS. 16-18). The first leg 540 is positioned within the recesses 543 on the first side 550 of the holder 508 and the second leg 541 is positioned within the recesses 544 on the second side 551 of the holder 508 (see, e.g., FIGS. 20-21).

The following example procedures may be carried out as part of performing a microarray test.

1) Properly position the holder 508 on the temperature control component 509 so that the beams illuminate the active area on the lower planar surface of the optical substrate 505 and CCD camera 510 is able to capture images of the whole active area of reaction chamber 506.

2) Glue the holder 508 at the proper position on the temperature control component 509 using thermally conductive glue. In some procedures, the next operation is not performed until the glue is dried.

3) Cut a piece of thermally conductive interface material such that the thermally conductive interface material has the same dimensions as that of reaction chamber 506. Place the thermally conductive interface material on the holder 508. The thermally conductive interface material may have to be replaced quite often.

4) Place the microarray 504 onto the thermally conductive interface material making sure that the first, second and/or third sides 521, 523, 525 of the microarray 504 are positioned against the respective first, second and/or third baffles 520, 522, 524 of the holder 508.

5) Apply pressure to the microarray 504 to adequately secure the microarray 504 to the thermally conductive interface material.

6) Secure the microarray 504 within the holder 508. In the example embodiment shown in FIGS. 14-15, one or more pins 426, 427 may be placed on to cylindrical projections 533 on a first side 530 of the holder 508 and then the respective hooks 535 of the pins 426, 427 may be manipulated under the protrusions 534 on a second side 532 of the holder 508. In the example embodiment shown in FIGS. 20-21, the pin 526 is a U-shaped member 526 such that the first leg 540 of the U-shaped member 526 is positioned within the recesses 543 on a first side 550 of the holder 508 and the second leg 541 of the U-shaped member 526 is positioned within the recesses 544 on the second side 551 of the holder 508.

The microarray readers 500 described herein may provide a simple and low-cost solution to overcome the drawbacks with existing microarray readers such as (i) improper alignment of the microarray on the temperature control component; (ii) an inadequately secured microarray which may cause shaking/trembling during optical scanning; and (iii) uneven temperature distribution across the buffer solution.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A microarray reader, comprising:
   a light source that emits light;
   beam shaping elements positioned near the light source to direct the light;
   a moving stage supporting the light source and beam shaping elements;
   a microarray that includes an optical substrate and a reaction chamber in contact with the optical substrate;
   a buffer solution encapsulated by the optical substrate and the reaction chamber;
   a holder that aligns the microarray relative to the light source such that when light hits the buffer solution certain molecules in the buffer solution are excited to emit fluorescent light;
   a temperature control component thermally engaged with the holder such that the temperature control component adjusts the temperature of the buffer solution;
   a sensor that receives the fluorescent light emitted by the excited molecules in the buffer solution to generate a signal;
   wherein the holder includes a first baffle that engages a first side of the microarray when the microarray is appropriately positioned within the holder;
   wherein the holder includes a second baffle that engages a second side of the microarray when the microarray is appropriately positioned within the holder; and
   wherein the holder includes a third baffle that engages a third side of the microarray when the microarray is appropriately positioned within the holder.

2. The microarray reader of claim 1, wherein a PCR reaction occurs within the buffer solution.

3. The microarray reader of claim 1, wherein the first baffle engages the optical substrate when the microarray is appropriately positioned within the holder.

4. The microarray reader of claim 3, wherein the second baffle engages the optical substrate when the microarray is appropriately positioned within the holder.

5. The microarray reader of claim 1, wherein the third baffle engages the optical substrate when the microarray is appropriately positioned within the holder.

6. A microarray reader, comprising:
   a light source that emits light;
   beam shaping elements positioned near the light source to direct the light;

a moving stage supporting the light source and beam shaping elements;

a microarray that includes an optical substrate and a reaction chamber in contact with the optical substrate;

a buffer solution encapsulated by the optical substrate and the reaction chamber;

a holder that aligns the microarray relative to the light source such that when light hits the buffer solution certain molecules in the buffer solution are excited to emit fluorescent light;

a temperature control component thermally engaged with the holder such that the temperature control component adjusts the temperature of the buffer solution;

a sensor that receives the fluorescent light emitted by the excited molecules in the buffer solution to generate a signal; and a pin that compresses the microarray against the holder.

7. The microarray reader of claim 6, wherein the pin engages the holder and the optical substrate.

8. The microarray reader of claim 6, wherein the pin is rotatably connected to a first side of the holder and engaged with a projection on an opposing second side of the holder.

9. The microarray reader of claim 8, wherein the holder includes a cylindrical projection on the first side of holder and the pin includes a cylindrical opening that receives the cylindrical projection such that the pin is rotatably connected to the first side of the holder.

10. The microarray reader of claim 9, wherein the holder includes a protrusion on the opposing second side of holder and the pin includes a hook that engages the protrusion to compress the microarray against the holder.

11. The microarray reader of claim 8, further comprising at least one additional pin that compresses the microarray against the holder.

12. The microarray reader of claim 6, wherein the pin is a U-shaped member.

13. The microarray reader of claim 6, wherein the U-shaped member includes a first leg, a second leg and a member that extends between the first leg and the second leg, the holder including recesses on a first side of the holder and recesses on second side of the holder, wherein the first leg is positioned within the recesses on the first side of the holder and the second leg is positioned within the recesses on the second side of the holder.

* * * * *